United States Patent [19]
Kreidl et al.

[11] Patent Number: 4,839,362
[45] Date of Patent: Jun. 13, 1989

[54] EBURNAMENINE DERIVATIVES, PHARMACEUTICAL COMPOSITIONS AND METHODS EMPLOYING THEM AND PROCESSES FOR THEIR PREPARATION

[75] Inventors: János Kreidl; György Visky; László Czibula; Béla Stefkö; Mária Farkas née Kirják; Zsolt Szombathelyi; Egon Kárpáti, all of Budapest; Béla Kiss, Vecsés; Katalin Csomor, Budapest; László Szporny, Budapest; Lilla Forgács, Budapest; Csaba Kuthi, Budapest; Anikó Gere, Budapest, all of Hungary

[73] Assignee: Richter Gedeon Vegyeszeti Gyar Rt., Budapest, Hungary

[21] Appl. No.: 853,844

[22] Filed: Apr. 18, 1986

[30] Foreign Application Priority Data

Apr. 19, 1985 [HU] Hungary .............................. 1516/85

[51] Int. Cl.$^4$ .................. A61K 31/475; C07D 461/00
[52] U.S. Cl. ...................................... 514/283; 546/51
[58] Field of Search .......................... 546/51; 514/283

[56] References Cited

U.S. PATENT DOCUMENTS

| | | | |
|---|---|---|---|
| 3,925,392 | 12/1975 | Najer et al. ............................ | 546/51 |
| 3,987,049 | 10/1976 | Plat et al. ............................... | 546/51 |
| 4,057,550 | 11/1977 | Szántay et al. ......................... | 546/51 |
| 4,065,458 | 12/1977 | Lörincz et al. ......................... | 546/51 |
| 4,120,858 | 10/1978 | Clauder et al. ......................... | 546/51 |
| 4,474,960 | 10/1984 | Szántay et al. ......................... | 546/70 |

FOREIGN PATENT DOCUMENTS

| | | | |
|---|---|---|---|
| 2703920 | 8/1977 | Fed. Rep. of Germany . | |
| 2035784 | 12/1970 | France .............................. | 514/283 |
| 2285390 | 4/1976 | France .............................. | 546/51 |

OTHER PUBLICATIONS

Toth, et al., Chemical Abstracts, vol. 93:239740y (1980).
Czira, et al., Chemical Abstracts, vol. 102:185332a (1985), Abstract of Org. Mass. Spectrom., 1984, 19(11), pp. 555–562.
Chemical Abstracts, 1982–1986 Chem. Substance Index, p. 24693CS.

*Primary Examiner*—Anton H. Sutto
*Assistant Examiner*—Diana G. Rivers
*Attorney, Agent, or Firm*—Herbert Dubno; Jonathan Myers

[57] ABSTRACT

The invention relates to the preparation of cis and trans stereoisomers of racemic and optically active eburnamenine derivatives of the general formula (Ia)

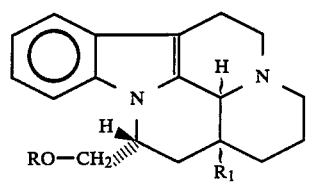

(Ia)

or (Ib),

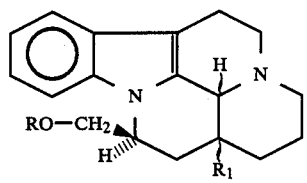

(Ib)

wherein
R$_1$ stands for a C$_{1-4}$ alkyl group; and
R stands for hydrogen, a C$_{1-6}$ alkyl group, a C$_{2-6}$ alkenyl group, an acyl or substituted acyl group,
as well as their acid addition salts, of which the trans compounds are novel.

The invention also relates to the compounds of the general formula (IIIa)

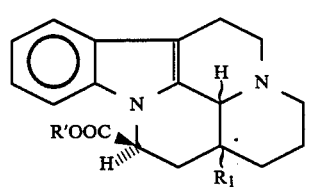

(IIIa)

and (IIIb),

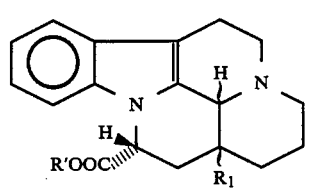

(IIIb)

wherein R$_1$ and R′ represent a C$_{1-4}$ alkyl group.

The compounds of the general formulae (Ia) and (Ib) possess a vasodilatory effect which is substantially higher than that of pentoxifyllin, a known peripheral vasodilator.

8 Claims, No Drawings

EBURNAMENINE DERIVATIVES, PHARMACEUTICAL COMPOSITIONS AND METHODS EMPLOYING THEM AND PROCESSES FOR THEIR PREPARATION

The invention relates to a novel process for the preparation of partially known, optically active eburnamenine derivatives of the formula (Ia)

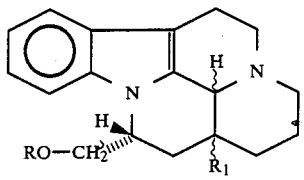
(Ia)

or (Ib).

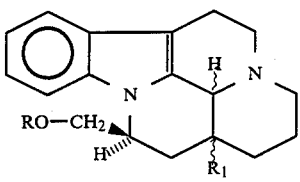
(Ib)

wherein
$R_1$ stands for a $C_{1-4}$ alkyl group;
R stands for hydrogen, a $C_{1-6}$ alkyl group, a $C_{2-6}$ alkenyl group, an acyl or substituted acyl group,
as well as their racemates and acid addition salts.

According to the invention the process for the preparation of the compounds of the formula (Ia) or (Ib) and their acid addition salts comprises (a$_1$) reducing an apovincaminic acid ester of the formula (IV),

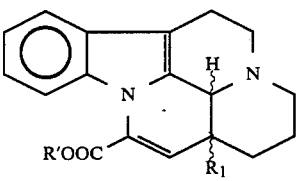
(IV)

wherein
$R_1$ is as defined above and
R' stands for a $C_{1-4}$ alkyl group,
by using a chemical reducing agent, preferably a complex metal hydride, then saturating by catalytic hydrogenation, if desired after acylating or alkylating, the thus-obtained compound of the formula (II),

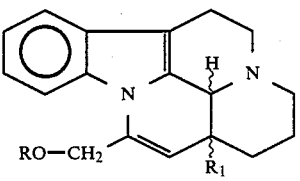
(II)

wherein
$R_1$ is as defined above and
R stands for hydrogen and, if desired, acylating or alkylating the thus-prepared compound of the formula (Ia), wherein $R_1$ is as defined above and R stands for hydrogen, or (a$_2$) saturating by catalytic hydrogenation, if desired after acylating or alkylating, an apovincaminol derivative of the formula (II), wherein $R_1$ is as defined above and R stands for hydrogen and, if desired, acylating or alkylating the thus-prepared compound of the formula (Ia), wherein $R_1$ is as defined above and R stands for hydrogen, or (b$_1$) saturating by catalytic hydrogenation a trans-apovincaminic acid ester of the formula (IV), wherein $R_1$ and R' are as defined above, then epimerizing the thusobtained product of the formula (IIIa),

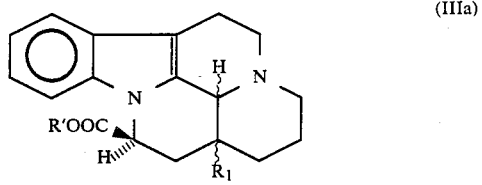
(IIIa)

wherein $R_1$ and R' are as defined above, and reducing the thus-prepared compound of the formula (IIIb),

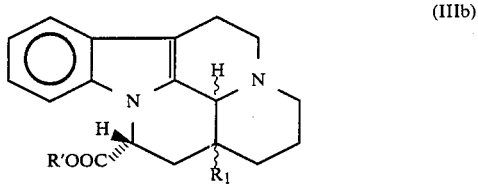
(IIIb)

wherein $R_1$ and R' are as defined above, by using a chemical reducing agent, preferably a complex metal hydride and, if desired, acylating or alkylating the thus-obtained compound of the formula (Ib), wherein $R_1$ is as defined above and R stands for hydrogen, or (b$_2$) saturating by catalytic hydrogenation a cis-apovincaminic acid ester of the formula (IV), wherein $R_1$ and R' are as defined above, separating the thus-obtained cis epimeric mixture by fractional crystallization, reducing the obtained product of the formula cis-(IIIa) or cis-(IIIb) by a chemical reducing agent, preferably by a complex metal hydride, after an "if desired" epimerization of the product of the formula (IIIa) and, if desired, acylating or alkylating the thus-prepared compound of the formula cis-(Ia) or cis-(Ib), wherein $R_1$ is as defined above and R means hydrogen, in order to prepare cis-stereoisomers forming a narrower group of the compounds of the formula (Ia) and (Ib), or (b$_3$) epimerizing a dihydroapovincaminic acid ester of the formula (IIIa), wherein $R_1$ and R' are as defined above, reducing the thus-obtained product of the formula (IIIb), wherein $R_1$ and R' are as defined above, by using a chemical reducing agent, preferably a complex metal hydride and, if desired, acylating or alkylating the thus-prepared compound of the formula (Ib), wherein $R_1$ is as defined above and R stands for hydrogen, or (b$_4$) reducing a dihydroapovincaminic acid ester of the formula (IIIb), wherein $R_1$ and R' are defined above, by using a chemical reducing agent, preferably a complex metal hydride, and, if desired, acylating or alkylating the thus-obtained product of the formula (Ib), wherein $R_1$ is defined above and R stands for hydrogen, or (c₁) reducing a dihydroapovincaminic acid ester of the formula (IIIa), wherein $R_1$ and R' are defined above, by using a chemical reducing agent, preferably by a complex metal hydride, and, if desired, acylating or alkylating the thus-obtained product of the formula (Ia), wherein $R_1$ is defined above and R represents hydrogen, and, if desired, converting the compounds of the formulae (II), (IIIa), (IIIb), (Ia) or (Ib) obtained by using any one of the above processes (a₁), (a₂), (b₁), (b₂), (b₃), (b₄) or (c₁) into their acid addition salts.

The annellation of the C/D rings in the compounds of the formula (Ia) and (Ib) may be cis or trans. The spatial position of the hydrogen atom at $C_3$ is cis in relation to the $R_1$ group at $C_{16}$ when the annellation is cis, whereas it is trans in the case of trans annellation. The hydrogen atom and the —CH₂—OR group at $C_{14}$ may be either axial or equatorial.

In the formulae $R_1$ and R' as $C_{1-4}$ alkyl groups may stand for straight or branched chain alkyl groups, e.g. methyl, ethyl, n-propyl, isopropyl, n-butyl, secondary butyl or tertiary butyl group, preferably methyl or ethyl; R as a $C_{1-6}$ alkyl group may represent an n-pentyl or n-hexyl group in addition to the meaning of the $R_1$ group; R may stand for the iso and/or branched chain analogs of these groups.

R may be as a $C_{2-6}$ alkenyl group the unsaturated analogs of these groups; as an acyl group it may represent an aliphatic acyl group, e.g. an acetyl, propionyl, butyryl or hexanoyl group; or an aromatic acyl group, e.g. benzoyl or naphthoyl group; as a substituted acyl group it may represent an acyl group substituted at the aromatic ring, e.g. a trimethoxybenzoyl, 4-chlorobenzoyl or 2-chlorobenzoyl group.

The trans derivatives of the formulae (II), (Ia) and (Ib) prepared according to the process of the invention are new compounds. The compounds of the formulae trans-(Ia) and trans-(Ib) are represented by the general formulae (Ia'), (Ia''), (Ib') and (Ib'').

pounds of the formula (Ia) or (Ib) or their therapeutically acceptable acid addition salts.

The cis-apovincaminol of the formula (II) containing an ethyl group as $R_1$ and hydrogen as R, as well as the corresponding hydrated cis-dihydroapovincaminols of the formulae (Ia) and (Ib) containing an ethyl group as $R_1$ and hydrogen as $R_2$, their acylated derivatives and the preparation of these compounds have first been reported in the French patent specification No. 2 035 784. According to this specification cis-apovincaminol is prepared by reducing apovincamine with lithium aluminum hydride in tetrahydrofuran and then acylating the thus-obtained alcohol with an appropriate acylating agent. Cis-dihydroapovincaminol is obtained from cis-vincaminol by using the process of M. Plat et al. (Bull. Soc. Chim. 1965, 2497) such that cis-vincaminol is heated in acetic acid at 100° C. for 4 hours and the aldehyde derivative obtained is reduced by a complex alkaline metal hydride. This reduction is carried out either by using sodium borohydride in an alcohol such as ethanol or methanol in a lasting several hours. The thus-obtained cis-dihydroapovincaminol is a mixture of epimers which can be separated by column chromatography. After the separation, the individual epimers are acylated with an appropriate acylating agent, e.g. acetic anhydride. According to this method, the epimeric mixture can also be acylated and the mixture of the acylated epimers can be separated by column chromatography.

According to said French patent specification, cis-apovincaminol and cis-dihydroapovincaminol derivatives are in general terms active on the circulatory and central nervous system, however these statements are not supported by pharmacological data.

The starting material for the process described in said French patent specification is cis-vincaminol which can be prepared from cis-vincamine only with difficulties. The reaction starting from cis-vincaminol is not stereoselective; thus, the epimers formed have to be separated by the means of column chromatography which is cumbersome for industrial purposes.

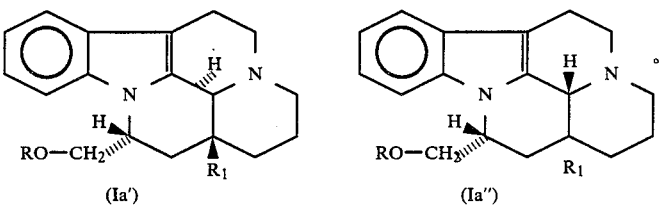

(Ia')  (Ia'')

(Ia)

(Ib)

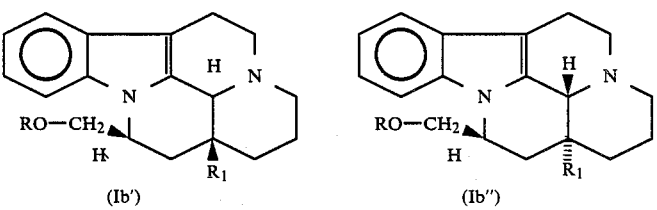

(Ib')  (Ib'')

The compounds of the formulae (Ia) and (Ib) are therapeutically active, particularly they possess peripheral vasodilatory action. Thus, the invention also relates to pharmaceutical compositions containing the com- The compounds of the formulae (IIIa) and (IIIb) are new. The racemic trans-14,15-dihydroeburnamenine derivatives which are prepared by reducing the appropriate 3,4-dehydroeburnamenine derivatives, are disclosed in the Hungarian patent specification No. 171,163. The configuration of the groups at $C_{14}$ is not mentioned in this specification; however, according to the nature of this reaction, one racemate of the trans-derivative can only be formed.

The new compounds of the formulae (IIIa) and (IIIb) are, on the one hand, valuable intermediates for process $b_1$) of the invention and, on the other hand, they can be used as starting materials for preparing other pharmacologically active substances.

As a contrast to the above described known processes, it has been found that the known cis and the novel trans stereoisomers can be prepared from the apovincaminic acid ester derivatives of the formula (IV) in good yields by using the processes of the invention and even stereoselectively in the case of substances of the formulae (IIIa), (IIIb), (Ia) and (Ib) containing an epimeric center. A further advantage appears in that the intermediate dihydroapovincaminic acid ester of the formula (IIIa) can completely be epimerized to the other diastereomer which makes possible to prepare any of the epimers of the formula (Ia) or (Ib) in a pure state with a good yield by using a simple crystallization.

The preparation of the apovincaminic acid ester derivatives of the formula (IV), wherein $R_1$ and $R'$ stand for a $C_{1-4}$ alkyl group, is described in our pending Hungarian patent application No. 1753/81 (U.S. Ser. No. 397,676, filed June 11, 1982, now U.S. Pat No. 4,474,960). According to this patent application, these compounds are obtained by treating a hydroxyimino-octahydroindolo[2,3-a]quinolizine derivative with a concentrated mineral acid or with an organic aliphatic or aromatic sulphonic acid in an inert organic solvent.

The new optically active trans stereoisomers of the formulae (Ia) and (Ib) (prepared according to any of the processes according to the invention) show valuable therapeutic action, particularly they possess a peripheral vasodilatory effect.

The vasodilatory action of the substances were studied on anaesthetized dogs. Hellige type electromagnetic flow meter heads were placed to the femoral and internal carotid artery of the animals and the amount of blood flowing through the vessel was measured. The mean arterial pressure was determined by using a Statham transducer connected to a polyethylene cannula introduced to the artery. The heart rate was measured from the pulsatory component of the blood pressure by using a frequency counter. All the values determined were continuously registered on a multichannel polygraph.

The effect of each compound was studied on several animals. On the intravenous (iv.) administration of the substances, the starting base-line values and the maximum change were evaluated.

Among the circulatory parameters studied, the heart rate and the carotid (central) blood flow were not influenced by the administered doses of the new trans derivatives investigated. A particularly outstanding effect was found on the increase in the blood flow of the femoral (extremital) arteries. For comparison, the action of pentoxifyllin (Trental$^R$) having a different chemical structure and used successfully as an extremital vasodilator in the therapy was also investigated. The results obtained are summarized in Table 1.

TABLE 1

The effect of the investigated compounds on the blood flow of the femoral artery on intravenous administration

| Compound | Dose mg/kg | No. of animals | Blood flow (blood amount flowing through the vessel) ml/min | | | Duration of the effect, min. |
| --- | --- | --- | --- | --- | --- | --- |
| | | | Before administration | Maximum change after administration | % | |
| (−)-3R,16S,14S—14,15-dihydro-14-hydroxy-methyl-eburnamenine (Example 18) | 1.0 | 4 | 50.5 | 53.7 | +6.3 | 0.25 |
| (+)-3R,16S,14R—14,15-dihydro-14-hydroxy-methyl-eburnamenine (Example 17) | 1.0 | 4 | 47.5 | 53.2 | +12 | 1.0 |
| (+)-3S,16R,14S—14,15-dihydro-14-hydroxy-methyl-eburnamenine (Example 4) | 1.0 | 2 | 30.0 | 52.5 | +75 | 2.0 |
| (−)-3S,16R,14R,14,14-dihydro-14-hydroxy-methyl-eburnamenine (Example 3) | 0.1 | 8 | 41 | 104 | +154 | 1.5 |
| | 1.0 | 8 | 42 | 116 | +176 | 11.0 |
| Pentoxifyllin | 1.0 | 5 | 32.4 | 33.4 | +3.1 | 1.9 |

It is obvious from the results illustrated in the Table that the peripheral vasodilatory effect of the compounds of the invention substantially exceeds the effect of pentoxifyllin known as an advantageous peripheral vasodilatory compound.

The values of duration of the effect are very remarkable: the compounds described in Example 3, when given in the same dose, possesses an action lasting much longer than that of pentoxifyllin. When compared to pentoxifyllin, an increase by 154% in the blood flow was observed in a dose ten times lower than that of pentoxifyllin with the same duration of the effect.

The invention is described in detail as follows.

In the process ($a_1$) an apovincaminic acid ester of the formula (IV) is reduced by using a chemically reducing agent, preferably a complex metal hydride. This reaction is carried out in an aprotic polar solvent, e.g. tetrahydrofuran, ethyl ether, diisopropyl ether, ethylene glycol dimethyl ether, suitably in tetrahydrofuran at a temperature between −70° C. and +20° C., preferably between −18° C. and +20° C. If desired, the thus-obtained apovincaminol of the formula (II) is acylated or alkylated and/or saturated by catalytic hydrogenation. Metals such as palladium, platinum as well as their oxides may be used as hydrogenating catalyst. The catalytic hydrogenation may also be accomplished in the presence of catalysts previously precipitated on the surface of a supporting material such as active carbon, silicon dioxide or aluminum oxide. Preferably, platinum (IV) oxide is used and the hydrogenation is carried out in a medium containing an alcohol, suitably methanol, ethanol or aqueous alcohol, conveniently in the presence of a strong inorganic or organic acid, e.g. hydrochloric, acetic or propionic acid at a temperature between 20° C. and 60° C., preferably at room temperature. Pressures between 1 and 10 atmospheres may be used.

After carrying out the catalytic hydrogenation, a compound of the formula (Ia) is obtained which contains an axial hydrogen atom and an equatorial —CH$_2$—OR group at C$_{14}$. As a result of the reaction, 2 to 3% of the epimer are also obtained which is, however, practically undetectable after working up the reaction mixture e.g. by recrystallization. When an apovincaminol derivative is used as starting material for the catalytic hydrogenation, the dihydroapovincaminol derivative of the formula (Ia) obtained can, if desired, be acylated or alkylated.

The apovincaminol derivatives of the formula (II) containing a hydrogen atom as R as well as the dihydroapovincaminol derivatives of the formula (Ia) containing a hydrogen atom as R can be acylated in a known manner by using a suitable acylating agent. When an acyl chloride, e.g. benzoyl chloride, is used as acylating agent, the acylation is performed in a solvent commonly used for acylating reactions with acyl chlorides, e.g. in a chlorinated hydrocarbon such as chloroform, dichloroethane, or in an aromatic hydrocarbon such as benzene or toluene, optionally in the presence of an acid binding agent, such as triethyl amine. This reaction is carried out at the boiling point of the solvent used.

When an acid anhydride, e.g. acetic or propionic anhydride, is used as acylating agent, the acylation is accomplished in an excess of the anhydride or in the presence of a solvent by adding the appropriate amount of the acid anhydride used for acylation. In this case the solvents commonly used for acylation with acyl chlorides may be employed. Similarly to the acylation with acyl chlorides, this reaction is also carried out at the boiling temperature of the acid anhydride or of the acid anhydride-solvent mixture.

The alkylation is performed in an aprotic polar or in an aprotic non-polar solvent, preferably in tetrahydrofuran or toluene at a temperature between the room temperature and the boiling point of the solvent used, suitably at the boiling point of the mixture. The alkylation is carried out by using alkyl halides, e.g. ethyl bromide or allyl bromide, in such a way that before adding the alkylating agent, the apovincaminol or dihydroapovincaminol derivative is converted in a known manner to an alkoxide in situ by using an alkaline metal hydride such as sodium hydride. This conversion is performed at a temperature between room temperature and the boiling point of the solvent used, preferably at the boiling point of the mixture, thereafter the alkylation can be started.

If desired, the compounds of the formula (II) or (Ia) obtained by the process (a$_1$) may be converted into their acid addition salts.

The process (a$_2$) is a part of the process (a$_1$) starting from a compound of the formula (II), the following steps of which are the same as in process (a$_1$).

In the course of the process (b$_1$), apovincaminic acid ester of the formula (IV) is saturated by catalytic hydrogenation. This hydrogenation may conveniently be accomplished in the presence of a 5 to 10% palladium-on-carbon, in an alcoholic solvent such as methanol or ethanol by using elemental hydrogen or any other hydrogen source, preferably formic acid. The suitable temperature of the hydrogenation is between room temperature and 60° C.; a temperature of about 40° C. is advantageous. A great advantage of this method consists in that a singly epimeric dihydroapovincaminic acid derivative, namely the compound of the formula (IIIa) containing an axial alkoxycarbonyl group is formed under kinetically controlled conditions. The compound of the formula (IIIa) may quantitatively be epimerized in a known way to the dihydroapovincaminic acid ester of the formula (IIIb) containing an equatorial alkoxycabonyl group in an alcoholic medium, preferably in the alcohol corresponding to the meaning of the group R', in the presence of a catalytic amount of a basic catalyst, suitably an alkaline metal alkoxide such as lithium, sodium or potassium alkoxide. The compounds of the formulae (IIIa) and (IIIb) may be separated as such or, if desired, converted to their acid addition salts. In addition to the use in the process of the invention, these compounds may be valuable intermediates for the preparation of other therapeutically useful drugs.

The dihydroapovincaminol derivatives of the formula (Ib) containing an axial hydroxymethyl group are obtained by reducing a compound of the formula (IIIb) with a complex metal hydride, preferably with aluminium hydride, in an aprotic polar solvent, suitably in tetrahydrofuran. This reduction proceeds with inversion. This transformation is carried out similarly to the preparation of the compounds of the formula (II) by using the process (a$_1$). The dihydroapovincaminol derivatives of the formula (Ib) can by acylated or alkylated as described in process (a$_1$) and/or transformed to their acid addition salts.

In the course of the process (b$_2$) a cis-apovincaminic acid ester of the formula (IV) used as starting material is saturated by catalytic hydrogenation as described in the process (b$_1$). Both cis-dihydroapovincaminic acid esters are parallelly formed in this reaction which are the C$_{14}$ epimers. This epimeric substances may be separated by selective fractional crystallization. The "A" epimers corresponding to the formula (IIIb) are easily crystallizable from the alcohol corresponding to the R' group. The "B" epimers corresponding to the formula (IIIa) can be obtained by evaporating the mother liquors and are easily purified e.g. by recrystallization from diisopropyl ether. The "B" epimeric dihydroapovincaminic acid ester derivatives may be epimerized to the adequate "A" epimers by using the method described in the process (b$_1$).

The cis-apovincaminic acid esters can be transformed to the cis-dihydroapovincaminols falling within the scope of the compounds according to the formulae (Ia) and (Ib) as described in process (b$_1$). It has been observed that the reaction also proceeded with inversion: namely, a cis-dihydroapovincaminol containing an axial hydroxymethyl group is obtained from the "A" epimeric dihydroapovincaminic acid ester wherein the alkoxycarbonyl group is equatorial; whereas a cis-dihydroapovincaminol containing an equatorial hydroxymethyl group is results from the "B" epimer containing an axial alkoxycarbonyl group.

If desired, the cis-dihydroapovincaminic acid ester derivatives obtained in the process (b₂) may be separated as described in process (b₁) or may be transformed to their acid addition salts. Similarly, the cis-dihydroapovincaminol derivatives obtained from the above compounds may be, if desired, acylated or alkylated according to the process (b₁) or may be converted to their acid addition salts.

In the course of the process (c₁), a dihydroapovincaminic acid ester of the formula (IIIa) containing an axial alkoxycarbonyl group is reduced with a complex metal hydride, preferably lithium aluminum hydride, in an aprotic polar solvent, suitably in tetrahydrofuran, to give with inversion a dihydroapovincaminol derivative of the formula (Ia) containing an equatorial hydroxymethyl group. This latter substance can be acylated or alkylated and/or transformed to an acid addition salt. The reduction, acylation and alkylation may be accomplished as described above in process (a₁).

The compounds of the formulae (II), (IIIa), (IIIb), (Ia) and (Ib) obtained by using the processes (a₁), (b₁) and (c₁) of the invention may be separated by filtering out the catalyst or the residues of any chemically reducing agent from the reaction mixture, evaporating the thus-obtained solution, mixing the residue with a water-immiscible solvent such as dichloromethane, chloroform, dichloroethane, benzene or toluene, then, if desired, making alkaline by adding 5% sodium carbonate soluton, separating, washing with water and finally evaporating after drying. The crude product obtained as an evaporation residue may be, if desired, purified by recrystallization.

The compounds of the formulae (II), (IIIa), (IIIb), (Ia) or (Ib) arising from any reaction step of the processes (a₁), (b₁), (b₂) or (c₁) according to the invention may be converted, if desired, to their acid addition salts. These salts can be formed in an inert solvent, e.g. in a $C_{1-6}$ aliphatic alcohol or in an aprotic polar solvent such as ether or acetone by dissolving a compound of the formula (II), (IIIa), (IIIb), (Ia) or (Ib) in the above solvent and adding an apropriate acid or the solution of this acid to the above solution until the pH value of the mixture becomes mildly acidic. Thereafter, the precipitated acid addition salt is separated from the reaction mixture by any suitable method, e.g. by filtration.

The active substances of the formula (Ia) or (Ib) can be converted into pharmaceutical compositions by mixing them with the usual non-toxic, inert, solid or liquid carriers and/or auxiliary agents which are commonly used in compositions suitable for enteral or parenteral administration. As carriers e.g. water, gelatine, lactose, starch, pectin, magnesium stearate, stearic acid, talc and vegetable oils such as peanut oil or olive oil or the like can be employed. The active ingredient can be formulated to the usual pharmaceutical compositions, particularly to solid forms such as rounded or angled tablets, dragées, capsules, e.g. gelatine capsules, pills, suppositories or the like. The amount of the solid materials can vary between wide limits, preferably they are used in an amount between about 25 mg and 1 g. The compositions may optionally contain the commonly used pharmaceutical additives, e.g. preserving agents, stabilizers, wetting agents, emulsifying agents or the like.

The pharmaceutical compositions are prepared by using the common methods involving e.g. sieving, mixing, granulating and pressing. The compositions may be subjected to further operations (e.g. sterilization) commonly used in the pharmaceutical industry.

The invention is illustrated in detail by the aid of the following non-limiting Examples.

EXAMPLE 1

Preparation of (−)-3S,16R,14S-14,15-dihydro-14-methoxycarbonyl-eburnaminene [a compound of the formula (IIIa)]

47 g. of (+)-3S,16R-14-methoxycarbonyl-eburnamenine are suspended in 380 ml. of methanol, flushed with nitrogen and 12 g. of a 10% palladium-on-carbon catalyst suspended in 50 ml. of dimethylformamide are added. After adding 25 ml. of formic acid to the suspension at room temperature, the mixture is stirred at 50° C. under nitrogen for 90 minutes. To the mixture 300 ml. of water are added, the catalyst is filtered off and washed with a total of 100 ml. of 50% aqueous methanol in two portions. After distilling off 300 ml. from the filtrate under reduced pressure, aqueous ammonia is added dropwise to the residue under vigorous stirring until reaching a pH value of 9. The precipitate is filtered, washed with water and then with distilled water until neutral and dried to give 47 g. of a crude product which is boiled with 100 ml. of methanol and the crystals are filtered off at 0° C. to give the title product in a yield of 42.5 g. (89.9%), m.p.: 217°–218° C., $[\alpha]_D^{20} = -178.4°$ (c=1.0, chloroform);

MS m/e: M⁺ 338, 337, 309, 279, 249;

¹H-NMR (CDCl₃/TMS): 0.63 t (3H) CH₃ Et; 2.82 s (1H) H-3; 3.68 s (3H) CH₃/COOCH₃; 4.87 d (1H) H-14 e; 6,93 m (1H) H-12; 7.09 m (2H) H-10,11; 7.48 ppm, m (1H) H-9.

¹³C-NMR (CHCl₃/TMS: C-2 132.1; C-3 67.8; C-5 53.0; C-6 35.5; C-7 105.8; C-8 128.0; C-9 119.3; C-10 120.5; C-11 118.1; C-12 109.8; C-13 137.0; C-14 53.8; C-15 32.1; C-16 35.3; C-17 21.14; C-18 21.14; C-19 56.1; C-20 18.5; C-21 6.8; CH₃O 52.0; CO 171.7.

EXAMPLE 2

Preparation of (+)-3S,16R,14R-14,15-dihydro-14-methoxycarbonyl-eburnamenine [a compound of the formula (IIIb)]

One g. of (−)-3S,16R,14S-14,15-dihydro-14-methoxycarbonyl-eburnamenine (prepared as described in Example 1) is dissolved in a solution of 0.1 g. of sodium in 50 ml. of absolute methanol and boiled under reflux for 2 hours, then 25 ml of methanol are distilled off under reduced pressure and 0.5 ml. of acetic acid is added to the residue. After evaporation to dryness, 50 ml. of chloroform and 15 ml. of water are added to the residue and the pH of the mixture obtained is adjusted to 9 by adding concentrated aqueous ammonia while stirring. The organic layer is separated, dried over anhydrous magnesium sulphate and, after filtration, the solution is evaporated to dryness. The remained pale yellow oil is boiled with 4 ml. of diisopropyl ether, the precipitated crystals are filtered off at 0° C. and washed with 0.5 ml. of cold diisopropyl ether to give the title compound in a yield of 0.8 g. (80%), m.p.: 113°–115° C., $[\alpha]_D^{20} = +71.7°$ (c=1.0, chloroform).

MS m/e: M⁺ 338, 337, 323, 309, 279, 249

¹H-NMR (CDCl₃/TMS): 0.78 t (3H) CH₃/Et; 3.02 s (1H) H-3; 3.83 s (3H) CH₃OOC; 4.65 d,d (1H) H-14 ax.; 7.02 m (1H) H-12; 7.13 m (2H) H-10,11; 7.45 ppm, m (1H) H-9

¹³C-NMR (CDCl₃/TMS): C-2 133.6; C-3 67.2; C-5 52.7; C-6 36.2; C-7 106.7; C-8 128.6; C-9 119.8; C-10 121.0; C-11 118.3; C-12 109.5; C-13 137.4; C-14 54.2;

C-15 31.9; C-16 36.0; C-17 21.6; C-18 21.5; C-19 55.8; C-20 18.9; C-21 7.1; CH$_3$O 52.44; CO 172.6.

EXAMPLE 3

Preparation of (−)-3S,16R,14R-14,15-dihydro-14-hydroxymethyl-eburnamenine [a compound of the formula (Ia)]

A solution containing 36.5 g. of (−)-3S,14S-14,15dihydro-14-methoxycarbonyl-eburnamenine (prepared as described in Example 1) in 700 ml of absolute tetrahydrofuran is cooled to −30° C. under nitrogen and 6 g. of lithium aluminium hydride are added. The temperature of the reaction mixture is allowed to warm to 0° C. during 15 minutes, then to 20° C. during additional 15 minutes. After stirring the mixture for one additional hour, 10 ml. of ethanol and then 10 ml. of water are dropwise added. The precipitate is filtered off at room temperature and washed with a total of 300 ml of chloroform in three portions in such a way that the precipitate is suspended in the boiling chloroform. The first filtrate containing tetrahydrofuran is evaporated to dryness under reduced pressure, the combined chloroformic washings are added to the residue and this mixture is extracted with 50 ml. of saturated sodium chloride solution. The organic phase is dried over anhydrous magnesium sulphate, filtered and evaporated to dryness under reduced pressure. The residue is boiled with 60 ml. of ethanol, the precipitated crystals are filtered off at 0° C. and washed with 10 ml. of cold ethanol to give the title compound in a yield of 30.8 g.

(92%), m.p.: 208°–209° C., $[\alpha]_D^{20} = -132.1°$ (c=1.0, chloroform).

MS m/e: 310, 309, 281, 279, 249

$^1$H-NMR (CDCl$_3$/TMS): 0.84 t (3H) CH$_3$/Et; 2.9 s (1H) H-3; 3.55 t (1H) H-14 ax.; 4.42 m (2H) CH$_2$-OH; 7.05 m (2H) H-10,11; 7.35 (1H) H-12; 7.45 ppm m (1H) H-9

$^{13}$C-NMR (CDCl$_3$/TMS): C-2 133.0; C-3 68.2; C-5 54.3; C-6 32.8; C-7 105.1; C-8 128.4; C-9 119.0; C-10 120.0; C-11 118.1; C-12 110.9; C-13 136.0; C-14 53.8; C-15 32.8; C-16 35.3; C-17 21.0; C-18 21.0; C-19 56.2; C-20 20.0; C-21 7.0; 7.0; CH$_2$OH 63.2.

EXAMPLE 4

Preparation of (+)-3S,16R,14S-14,15-dihydro-14-hydroxymethyl-eburnamenine [a compound of the formula (Ib)]

A solution containing 0.4 g of (+)-3S,16R,14R-14,15-dihydro-14-methoxycarbonyl-eburnamenine in 15 ml. of absolute tetrahydrofuran is cooled to −30° C. and 0.1 g. of lithium aluminium hydride is added under nitrogen. The temperature of the reaction mixture is allowed to warm to 20° C., the mixture is stirred at 20° C. for one hour, then 1 ml. of methanol and 0.5 ml. of water are added. The precipitate is filtered off and washed with a total of 40 ml. of boiling chloroform in two portions. The filtrate containing tetrahydrofuran is evaporated under reduced pressure to an oil, the combined chloroformic washings are added and this mixture is extracted with 10 ml. of saturated aqueous sodium chloride solution, dried over anhydrous magnesium sulphate, filtered and evaporated under reduced pressure. The oily residue is boiled with 2 ml. of diisopropyl ether, the precipitated crystals are filtered off at 0° C. and dried to give the title compound in a yield of 0.31 g.

(84.5%), m.p.: 165°–167° C., $[\alpha]_D^{20} = +26.9°$ (c=1.0, chloroform).

$^1$H-NMR (CDCl$_3$/TMS): 0.74 t (3H) CH$_3$/Et; 2.95 (1H) H-3; 3.8 d (1H) H-14 e; 4.3 m (2H) CH$_2$OH); 7.12 m (2H) H-10,11; 7.38 m (1H) H-12; 7.48 ppm m (1H) H-9.

$^{13}$C-NMR (CDCl$_3$/TMS): C-2 135.1; C-3 67.2; C-5 52.6; C-6 35.5; C-7 106.1; C-8 128.5; 119.3; C-10 120.5; C-11 118.3; C-12 110.0; C-13 136.8; C-14 52.7; C-15 32.3; C-16 35.1; C-17 21.7; C-18 21.5; C-19 55.8; C-20 19.3; C-21 7.3; CH$_2$OH 64.6.

EXAMPLE 5

Preparation of (−)-3S,16R-14-hydroxymethyl-eburnamenine [a compound of the formula (II)]

A solution containing 18 g. of (+)-3S,16R-14-methoxycarbonyl-eburnamenine in 500 ml. of absolute tetrahydrofuran is cooled to −50° C. under nitrogen and 5 g. of lithium aluminium hydride are added. The mixture is allowed to warm to 0° C. within 30 minutes, then 10 ml. of ethanol and 10 ml. of water are dropped to the mixture at 20° C. The precipitated is filtered off at 30° C. and washed with 100 ml. of hot tetrahydrofuran. The tetrahydrofuran solution is shaken with 100 ml. of saturated sodium chloride solution, the precipitated sodium chloride is filtered off, the phases are separated and the tetrahydrofuran phase is evaporated to dryness under reduced pressure. The residue is boiled with 20 ml. of ethanol, the crystalline precipitate is filtered off at 0° C. and washed with 5 ml. of cold ethanol to give the title compound in a yield of 14.85 g. (90%), m.p. 156°–157° C., $[\alpha]_D^{20} = -108.3°$ (c=1.0, chloroform).

EXAMPLE 6

Preparation of (−)-3S,16R,14R-14,15-dihydro-14-hydroxymethyl-eburnamenine [a compound of the formula (Ia)]

0.05 g. of a 80% platinum(IV) oxide catalyst is added to a solution containing 0.5 g. of (−)-3S,16R-14hydroxymethyl-eburnamenine (prepared as described in Example 5) in the mixture of 20 ml. of methanol and 5 ml. of glacial acetic acid. The reaction mixture is stirred in an autoclave under a pressure of 5 to 6 atmospheres at room temperature until the absorption of hydrogen ceases (2 hours). The system is flushed with nitrogen and the catalyst is filtered off. The solution obtained is evaporated to dryness, the residue is dissolved in 50 ml. of water and alkalinized to pH 9 by adding concentrated aqueous ammonia under stirring. The amorphous precipitate is filtered, dried and boiled with 2 ml. of ethanol. The crystalline precipitate is filtered off at 0° C. and washed with a little volume of cold ethanol to give the title compound in a yield of 0.4 g (80%), m.p.: 208°–209° C., $[\alpha]_D^{20} = -133.0°$ (c=1.0, chloroform).

The spectroscopic data of the title product are in accordance with those of the compound described in Example 3.

EXAMPLE 7

Preparation of (−)-3S,16R,14R-14,15-dihydro-14-acetoxymethyl-eburnamenine [a compound of the formula (Ia)]

5 ml. of acetic anhydride are added to a suspension of 1.0 g. of (−)-3S,16R,14R-14,15-dihydro-14hydroxymethyl-eburnamenine (prepared as described in Example 3) in 20 ml. of chloroform and the suspension is boiled under reflux for 2 hours. Thereafter, the mixture is evaporated to an oil under reduced pressure, the residue is dissolved in 50 ml. of water and alkalinized to pH 9 by adding aqueous ammonia while stirring. The mixture is stirred for one hour, the amorphous precipitate is filtered off, washed with distilled water until neutral and dried to give 1.0 g. of the product which is recrystallized from 4 volumes of diisopropyl ether to give the title compound in a yield of 0.9 g. (79.2%), m.p.: 153°–154° C., $[\alpha]_D^{20} = -68.5°$ (c = 1.0, chloroform). MS m/e: M+ 352, 351, 323, 309, 293, 279, 263, 249.

EXAMPLE 8

Preparation of (−)-3S,16R,14R 14,15-dihydro-14-allyloxymethyl-eburnamenine [a compound of the formula (Ia)]

0.5 g. of 80% sodium hydride is added to a solution of 1.55 g. of (−)-3S,16R,14R-14,15-dihydro-14-hydroxymethyl-eburnamenine (prepared as described in Example 3) in 30 ml. of absolute tetrahydrofuran, the mixture is boiled under reflux for one hour and after adding 0.7 ml. of freshly distilled allyl bromide, it is boiled under reflux for additional 2 hours. Then, after adding 2 ml. of methanol, the mixture is evaporated to dryness under reduced pressure. The residue is dissolved in 50 ml. of chloroform, washed with 10 ml. of saturated aqueous sodium chloride solution, the organic phase is dried over anhydrous magnesium sulphate, filtered and evaporated under reduced pressure. After boiling the oily residue with 3 ml. of methanol and cooling it to 0° C., the precipitate is filtered off to give the title compound in a yield of 1.5 g. (85.7%), m.p.: 115°–117° C., $[\alpha]_D^{20} = -126.2°$ (c = 1.0, chloroform).

EXAMPLE 9

Preparation of (+)-3S,16R,14R-14,15-dihydro-14-benzoyloxymethyl-eburnamenine hydrochloride [hydrochloride of a compound of the formula (Ia)]

5.5 ml. of benzoyl chloride and 6 ml. of triethylamine are added to a solution containing 8.2 g. of (−)-3S,16R14R-14,15-dihydro-14-hydroxymethyl-eburnamenine in 150 ml. of absolute benzene. The solution is boiled under reflux under nitrogen for 3 hours, then 100 ml. of water and 40 ml. of 10% sodium hydrogen carbonate solution are added at room temperature. The mixture is filtered through Celite, separated and the benzene layer is washed with 30 ml. of saturated aqueous sodium chloride solution and dried over anhydrous magnesium sulphate. After filtration the benzene solution is stirred with 0.5 g. of activated carbon at room temperature for one hour, then filtered and evaporated under reduced pressure. The oily residue is dissolved in 50 ml. of ether and the solution is acidified to pH 5 by adding hydrogen chloride dissolved in isopropanol. The precipitate is filtered, washed with 15 ml. of acetone and dried to give the title hydrochloride salt in a yield of 9.8 g. (82%), m.p.: 262°–265° C., $[\alpha]_D^{20} = +29.9°$ (c = 1.0, methanol).

EXAMPLE 10

Preparation of (+)-3S,16R,14R-14,15-dihydro-14-trimethoxybenzoyl-oxymethyl-eburnamenine [a compound of the formula (Ia)]

10 g. of trimethoxybenzoyl chloride and 7 ml. of triethyl amine are added to 7 g. of (−)-3S,16R,14R-14,15-dihydro14-hydroxymethyl-eburnamenine dissolved in 120 ml. of absolute benzene. The solution is boiled under reflux for 3 hours, then 100 ml. of water and 15 ml. of 10% sodium hydrogen carbonate solution are added and the mixture is filtered through Celite. After separation, the benzene layer is dried over anhydrous magnesium sulphate and evaporated to dryness under reduced pressure. After recrystallizing the residue from 20 ml. of diisopropyl ether, the crystalline precipitate is filtered off, washed with 5 ml. of cold diisopropyl ether and dried to give the title compound in a yield of 7.7 g. (67.6%), m.p.: 140°–141° C., $[\alpha]_D^{20} = +18.2°$ (c = 1.0, chloroform).

EXAMPLE 11

Preparation of (+)-3S,16R,14S-14,15-dihydro-14acetoxymethyl-eburnamenine [a compound of the formula (Ib)]

3 ml of acetic anhydride are added to a solution containing 0.5 g. of (+)-3S,16R,14S-14,15-dihydro-14-hydroxymethyl-eburnamenine (prepared as described in Example 4) in 20 ml. of chloroform and the solution is boiled under reflux for 2 hours. Thereafter, the mixture is evaporated to dryness and after dissolving the residue in 20 ml. of dichloromethane, 20 ml. of water and 2 ml. of 10% sodium hydrogen carbonate solution are added. After shaking the phases are separated and the organic solution is evaporated under reduced pressure. The oily residue is recrystallized from 2 ml. of diisopropyl ether and the precipitate is washed with a little volume of cold diisopropyl ether to give the title compound in a yield of 0.4 g., m.p.: 85°–87° C., $[\alpha]_D^{20} = +25.7°$ (c = 1, chloroform). MS m/e: M+ 352, 351, 323, 309, 279, 249.

EXAMPLE 12

Preparation of (−)-3S,16R-14-trimethoxybenzoyloxymethyleburnamenine [a compound of the formula (II)]

6.8 g. of trimethoxybenzoyl chloride and 5 ml. of triethyl amine are added to a solution containing 6 g. of (−)-3S,16R-14-hydroxymethyl-eburnamenine (prepared as described in Example 5) in 100 ml. of absolute benzene. The solution is boiled under reflux for 3 hours, 100 ml. of water and 10 ml. of 10% sodium hydrogen carbonate solution are added and the mixture is filtered through Celite. After separating the phases, the organic solution is dried over anhydrous magnesium sulphate and evaporated to dryness under reduced presssure. After recrystallizing the residue from 20 ml. of diisopropyl ether, the title compound is obtained in a yield of 5.6 g. (68.5%), m.p.: 114°–115° C., $[\alpha]_D^{20} = -45.4°$ (c = 1.0, chloroform).

EXAMPLE 13

Preparation of (−)-3S,16R-14-benzoyloxymethyl-eburnamenine [a compound of the formula (II)]

4 ml. of benzoyl chloride and 5 ml. of trimethyl amine are added to 6 g. of (−)-3S,16R-14-hydroxymethyleburnamenine (prepared as described in Example 5) dissolved in 100 ml. of absolute benzene. The solution is boiled under reflux for 3 hours and then 100 ml. of water and 15 ml. of 10% sodium hydrogen carbonate solution are added. After shaking the mixture is filtered through Celite, separated and the benzene phase is dried over anhydrous magnesium sulphate. After filtration the solution is evaporated under reduced pressure. After recrystallizing the oily residue from 12 ml. of diisopropyl ether, filtering the precipitate obtained after cooling and washing the precipitate with 2 ml. of cold diisopropyl ether, the title product is obtained in a yield of 7.2 g. (89.2%), m.p.: 113°–114° C., $[\alpha]_D^{20} = -97.2°$ (c = 1.0, chloroform).

EXAMPLE 14

Preparation of (+)-3R,16S-14,15-dihydro-14-ethoxycarbonyleburnamenine [a compound of the formula (IIIa)]

A solution containing 8 g. of (−)-3R,16S-14-ethoxycarbonyl-eburnamenine in 70 ml. of ethanol is flushed with nitrogen and 2 g. of 10% palladium-on-carbon suspended in 8 ml. of dimethylformamide are added. After adding 4 ml. of formic acid to the solution the mixture is stirred at 40° C. for 3 hours. Then, the catalyst is filtered off at 40° C. and the substance precipitated onto the catalyst is washed out at 60 to 70° C. by using 200 ml. of ethanol containing 15% of water in two portions. The filtrate is evaporated to one third of its original volume under reduced pressure, 70 ml. of dichloromethane and 100 ml. of water are added to the residue which is then alkalinized to pH 9 by adding aqueous ammonia under vigorous stirring. The organic layer is separated and the aqueous layer is extracted with 20 ml. of dichloromethane. The combined organic phase is dried over magnesium sulphate and evaporated. The residue is boiled with 10 ml. of ethanol, cooled to 0° C. and the precipitate is filtered off to give the title product in a yield of 7 g. (87.5%), m.p.: 172°–173° C., $[\alpha]_D^{20} = +175.5°$ (c=1.0, chloroform).

EXAMPLE 15

Preparation of (−)-3R,16S,14R-14,15-dihydro-14-ethoxycarbonyl-eburnamenine hydrochloride [hydrochloride of a compound of the formula (IIIb)]

After adding 0.1 g. of potassium tertiary butoxide to a solution containing 1.5 g. of (+)-3R,16S,14S-14,15-dihydro-14-ethoxycarbonyl-eburnamenine (prepared as described in Example 14) in 20 ml. of absolute ethanol, the mixture is boiled under reflux for 2 hours and then acidified to a pH value of 6 by adding acetic acid. The solution is evaporated to dryness, the residue is dissolved in 30 ml. of dichloromethane and extracted with 10 ml. of 2% sodium hydrogen carbonate solution. The organic phase is dried over anhydrous magnesium sulphate and evaporated under reduced pressure. The oily residue is dissolved in 3 ml. of ethanol and ethanolic hydrogen chloride solution is added until a pH value of 2 to 3 is reached. Thereafter, the mixture is cooled to 0° C., the precipitate is filtered out and washed with a little volume of cold ethanol to give the title hydrochloride in a yield of 1.0 g., m.p.: 239°–241° C., $[\alpha]_D^{20} = -80.4°$.

EXAMPLE 16

Preparation of (+)-3R,16S,14S-14,15-dihydro-14-methoxycarbonyl-eburnamenine [a compound of the formula (IIIa)]

The process described in Example 1 is followed except that (−)-3R,16S-14-methoxycarbonyl-eburnamenine is used as starting material to give the title compound in a yield of 43.2 g. (91.5%), m.p.: 219°–221° C., $[\alpha]_D^{20} = +181.5°$ (c=1.0, chloroform).

EXAMPLE 17

Preparation of (+)-3R,16S,14R-14,15-dihydro-14-hydroxymethyl-eburnamenine [a compound of the formula (Ia)]

The process described in Example 3 is followed, except that 3.65 g. of (+)-3R,16S,14S-14,15-dihydro-14-methoxycarbonyl-eburnamenine (prepared as described in Example 16) are used as starting material. (Of course, the amounts of the solvents and reactants are proportional.) The title compound is obtained in a yield of 3.2 g. (95.6%), m.p.: 204°–205° C., $[\alpha]_D^{20} = +132.4°$ (c=1.0, chloroform).

EXAMPLE 18

Preparation of (−)-3R,16S,14S-14,15-dihydro-14-hydroxymethyl-eburnamenine [a compound of the formula (Ib)]

After adding 10 ml. of water to a suspension containing 5 g. of (−)-3R,16S,14R-14,15-dihydro-14-ethoxycarbonyl-eburnamenine hydrochloride (prepared as described in Example 15) in 50 ml. of benzene, the mixture is alkalinized to pH 9 adding concentrated aqueous ammonia while vigorous stirring. After separation the organic phase is dried over anhydrous magnesium sulphate, the drying agent is filtered out and the filtrate is evaporated to dryness. The oily residue is dissolved in 80 ml. of absolute tetrahydrofuran and 0.8 g. of lithium aluminium hydride is added at a temperature of −30° C. Thereafter the mixture is allowed to warm slowly to 20° C. and stirred at 20° C. for one additional hour. After adding 4 ml. of methanol and 1 ml. of water to the mixture the precipitate is filtered off and washed with a total volume of 50 ml. of hot tetrahydrofuran in two portions. The tetrahydrofuran filtrates are combined and extracted with 20 ml. of saturated sodium chloride solution. The precipitated salt is filtered out and after separation, the tetrahydrofuran solution is evaporated. The residue is dissolved in 5 ml. of hot diisopropyl ether, filtered through Celite, the filtrate is cooled to −5° C. and the precipitate is filtered out to give the title compound of a yield of 2.87 g. (72%), m.p.: 169°–171° C., $[\alpha]_D^{20} = -24.3°$ (c=1.0, chloroform).

EXAMPLE 19

Preparation of (−)-3S,16R,14R-14,15-dihydro-14-propionyloxymethyl-eburnamenine [a compound of the formula (Ia)]

After adding 5 ml. of propionic anhydride to 1 g. of (−)-3S,16R,14R-14,15-dihydro-14-hydroxymethyl-eburnamenine (prepared as described in Example 3), the mixture is heated at 100° C. for 90 minutes under stirring, then 20 ml. of diisopropyl ether are added to the mixture and isopropanolic hydrogen chloride solution is added until the pH value of 1 is reached. The precipitated hydrochloride of the title compound is filtered off and washed with 5 ml. of diisopropyl ether to give the salt in a yield of 1.5 g. This salt is dissolved in 25 ml. of chloroform, thoroughly shaken with 10 ml. of 5% sodium hydrogen carbonate solution and the chloroformic solution is dried and evaporated. After recrystallizing the residue from 3 ml. of n-hexane, the title compound is obtained in a yield of 0.8 g., m.p.: 81° C., $[\alpha]_D^{20} = -63.2°$ (c=1.0, chloroform).

EXAMPLE 20

Preparation of the "A" and "B" epimers of 3S,16S-14,15-dihydro-14-ethoxycarbonyl-eburnamenine To a solution containing 50 g. of (+)-3S,16S-14-ethoxycarbonyl-eburnamenine in 375 ml. of ethanol, a suspension of 10 g. of 10% palladium-on-carbon catalyst in 40 ml. of dimethylformamide is added, then 25 ml. of formic acid are added dropwise to the suspension under stirring. The mixture is stirred at 40° C. for 4 hours while stirring, then the catalyst is filtered off at 40° C. and washed in two portions with a total volume of 150 ml. of 50% aqueous ethanol kept at 60° C. The combined filtrate is evaporated to 200 ml. under reduced pressure and after adding 300 ml. of dichloromethane and 200 ml. of water, the mixture is alkalinized to pH 9 by using concentrated aqueous ammonium hydroxide solution while stirring. The organic phase is separated and the aqueous layer is extracted with 50 ml. of dichloromethane. The organic phases are combined and evaporated to dryness.

(a) Separation of the "A" epimer: (+)-3S,16S,14R-14,15-dihydro-14-ethoxycarbonyl-eburnamenine [a compound of the formula (IIIb)]

After adding 100 ml. of ethanol, the evaporation residue is stirred at 15° C. for 2 hours. The crystalline precipitate is filtered off and washed twice with 5 ml. of cold ethanol to give the "A" epimer in a yield of 21.5 g., m.p.: 151°–154° C., $[\alpha]_D^{20} = +111.1°$ (c=1.0, chloroform).

(b) Separation of the "B" epimer: (−)-3S,16S,14S-14,15-dihydro-14-ethoxycarbonyl-eburnamenine [a compound of the formula (IIIa)]

150 ml. of distilled water are dropwise added to the mother liquor obtained above in (a) at room temperature while stirring. The solution becomes milky and crystallization soon begins. The mixture is stirred at −5° C. for 2 hours. The crystalline precipitate is filtered and washed twice with 5 ml. of 50% aqueous ethanol at 0° C. to give the crude "B" epimer in a yield of 26.2 g., m.p.: 88°–90° C., $[\alpha]_D^{20} = -89.9°$ (c=1, chloroform).

After recrystallizing the crude product from 50 ml. of diisopropyl ether, the pure "B" epimer is obtained in a yield of 20.4 g., m.p.: 91°–92° C., $[\alpha]_D^{20} = -102.8°$ (c=1.0, chloroform).

EXAMPLE 21

Preparation of (+)-3S,16S,14S-14,15-dihydro-14-hydroxymethyl-eburnamenine [a compound of the formula (Ib)]

4.75 g. of lithium aluminium hydride are portionwise added at −30° C. under nitrogen to a solution containing 17.7 g. of the compound prepared as described in Example 20 (a) in 475 ml. of absolute tetrahydrofuran and the mixture is allowed to warm to 0° C. while stirring for one hour. To this solution 10 ml. of ethanol and then 10 ml. of water are added while keeping the temperature at 20° C. The precipitate is filtered and washed with a total volume of 150 ml. of hot tetrahydrofuran in 3 portions. The combined tetrahydrofuran solution is washed with 150 ml. of saturated sodium chloride solution, filtered through 2 g. of Celite and the organic phase is carefully separated at 10° C. The solution is evaporated to dryness under reduced pressure, the residue is boiled with 12 ml. of ethanol and cooled to 0° C. The precipitate is filtered out and washed with 4 ml. of cold ethanol to give the title compound in a yield of 14.5 g. (92%), m.p.: 168°–169° C., $[\alpha]_D^{20} = +64.2°$ (c=1.0, chloroform).

EXAMPLE 22

Preparation of (−)-3S,16S,14R-14,15-dihydro-14-hydroxymethyl-eburnamenine [a compound of the formula (Ia)]

5 g. of lithium aluminium hydride are portionwise added under nitrogen at −30° C. to a solution containing 20 g. of the compound prepared as described in Example 20(b) in 500 ml. of absolute tetrahydrofuran and the mixture is allowed to warm to 0° C. while stirring for one hour. To this solution 10 ml. of ethanol and then 10 ml. of water are added while keeping the temperature at 20° C. The precipitate is filtered and washed with a total volume of 150 ml. of hot tetrahydrofuran in 3 portions. The combined tetrahydrofuran solution is washed with 150 ml. of saturated sodium chloride solution, filtered through 2 g. of Celite and the organic phase is carefully separated. The organic phase is evaporated to dryness under reduced pressure, the residue is boiled with 15 ml. of ethanol and then cooled to 0° C. The precipitate is filtered out and washed with 5 ml. of cold ethanol to give the title compound in a yield of 16 g. (90%), m.p.: 191°–193° C., $[\alpha]_D^{20} = -65.5°$ (c=1.0, chloroform).

EXAMPLE 23

Preparation of the "A" and "B" epimers of 3R,16R-14,15-dihydro-14-methoxycarbonyl-eburnamenine To a suspension containing 4 g. of (−)-3S,16S-14-ethoxycarbonyl-eburnamenine in 35 ml. of methanol, a suspension of 1.2 g. of 10% palladium-on-carbon catalyst in 5 ml. of dimethyl formamide is added, then 3 ml. of formic acid are dropped in. The mixture is stirred at 50° C. for 90 minutes, then the catalyst is filtered off and washed in 2 portions with a total volume of 20 ml. of 50% aqueous methanol at 40° C. The combined filtrate is evaporated to 20 ml. under reduced pressure and after adding 25 ml. of chloroform and 20 ml. of water to the residue, the mixture is alkalinized to pH 9 by using concentrated aqueous ammonia while stirring. After separation the aqueous phase is extracted with 20 ml. of chloroform, the chloroformic phases are combined, dried and after filtering off the drying agent, the solution is evaporated to dryness.

(a) Separation of the "A" epimer: (−)-3R,16R,14R-14,15-dihydro-14-methoxycarbonyl-eburnamenine [a compound of the formula (IIIb)]

The evaporation residue obtained above is boiled with 6.5 ml. of methanol, then the solution is cooled to 10° C., the crystalline precipitate is filtered off and washed with a little volume of cold methanol to give the "A" epimer in a yield of 1.2 g., m.p.: 157°–159° C., $[\alpha]_D^{20} = -113.2°$ (c=1.0, chloroform).

(b) Separation of the "B" epimer: (+)-3R,16R,14S-14,15-dihydro-14-methoxycarbonyl-eburnamenine [a compound of the formula (IIIa)]

The mother liquor obtained above in (a) is evaporated to dryness and the residue is boiled with 5 ml. of diisopropyl ether, then the mixture is cooled to 0° C. and kept at this temperature for 4 hours. The crystalline precipitate is filtered off and washed with a little volume of cold diisopropyl ether to give the "B" epimer in a yield of 2 g., m.p.: 69°–71° C., $[\alpha]_D^{20} = +108.4°$ (c=1.0, chloroform).

EXAMPLE 24

Preparation of (−)-3R,16R,14S-14,15-dihydro-14-hydroxymethyl-eburnamenine [a compound of the formula (Ib)]

0.24 g. of lithium aluminium hydride is portionwise added under nitrogen at −10° C. to a solution containing 1 g. of the compound prepared as described in Example 23(a) in 30 ml. of absolute tetrahydrofuran. After one hour 1 ml. of ethanol and the 1.0 ml. of water are added to the solution while keeping the temperature at 20° C. The precipitate is filtered off and washed with a total volume of 40 ml. of chloroform in 2 portions. The filtrate is combined with the washing liquid and evaporated to dryness. The residue is dissolved in 30 ml. of chloroform and extracted with 10 ml. of saturated sodium chloride solution. After separation the organic phase is dried over anhydrous magnesium sulphate, filtered and evaporated to dryness under reduced pressure. The residue is boiled with 2 ml. of ethanol and cooled to 0° C. The crystalline precipitate is filtered out and washed with a little volume of cold ethanol to give the title compound in a yield of 0.7 g. (76%), m.p.: 164°–167° C., $[\alpha]_D^{20} = -60.1°$ (c=1.0, chloroform).

EXAMPLE 25

Preparation of (+)-3R,16R,14R-14,15-dihydro-14-hydroxymethyl-eburnamenine [a compound of the formula (Ia)]

One g. of the product obtained as described in Example 23(b) is treated according to the process described in Example 24 to give the title product in a yield of 0.72 g. (79%), m.p.: 190°–192° C., $[\alpha]_D^{20} = +60.0°$ (c=1.0, chloroform).

EXAMPLE 26

Preparation of (+)-3S,16S,14S-14,15-dihydro-14-benzoyloxymethyl-eburnamenine [a cis compound of the formula (Ib)]

2 g. of benzoyl chloride and 3 ml. of absolute triethyl amine are added to a solution containing 4 g. of (+)-3S,16S,14S-14,15-dihydro-14-hydroxymethyl-eburnamenine in 70 ml. of absolute benzene. The mixture is boiled under reflux for 2 hours, then cooled to room temperature. After adding 100 ml. of water and sodium hydrogen carbonate the mixture is stirred until a constant pH value of 8.5. After adding 1 g. of Celite the mixture is filtered, the filtrate is separated and the benzene solution is evaporated to dryness under reduced pressure. After recrystallizing the oily residue from diisopropyl ether with the addition of activated carbon, the title compound is obtained in a yield of 4.8 g. (89.8%), m.p.: 75°–77° C., $[\alpha]_D^{20} = +9.9°$ (c=1.0, chloroform).

EXAMPLE 27

Preparation of (+)-3S,16S,14R-14,15-dihydro-14-benzoyloxymethyl-eburnamenine [a cis compound of the formula (Ia)]

5 g. of benzoyl chloride and 4.5 ml. of absolute triethyl amine are added to a solution containing 7.25 g. of (−)-3S,16S,14R-14,15-dihydro-14-hydroxymethyl-eburnamenine in 100 ml. of absolute benzene. The mixture is boiled under reflux for two hours and a half, then cooled to room temperature. After adding 100 ml. of water, sodium hydrogen carbonate is added in order to reach a constant pH value of 8.5 while stirring. After stirring for 30 minutes the benzene layer is separated and extracted with 50 ml. of saturated sodium chloride solution, dried and clarified by adding active carbon and Brockmann II aluminium oxide. After filtration the solution is evaporated to dryness under reduced pressure. After recrystallizing the residue from diisopropyl ether the title compound is obtained in a yield of 5.8 g. (60%), m.p.: 101°–103° C., $[\alpha]_D^{20} = +33.3°$ (c=1.0, chloroform).

EXAMPLE 28

Preparation of (−)-3S,16S,14S-14,15-dihydro-14-trimethoxybenzoyl-oxymethyl-eburnamenine hydrochloride [hydrochloride of a cis compound of the formula (Ib)]

6.8 g. of trimethoxybenzoyl chloride and 4.5 ml. of absolute triethyl amine are added to 6 g. of (+)-3S,16S,14S-14,15-dihydro-14-hydroxymethyl-eburnamenine dissolved in 100 ml. of absolute benzene. The mixture is boiled under reflux for 3 hours, then cooled to room temperature. After adding 100 ml. of water sodium hydrogen carbonate is added in order to reach a pH value of 8.5 while stirring. After filtering the mixture through 1 g. of Celite, the benzene phase is separated, dried and evaporated. [Recrystallization of the base from diisopropyl ether gives a poor yield, m.p.: 156°–158° C., $[\alpha]_D^{20} = -1.6°$ (c=1.0, chloroform)]. The oily residue is dissolved in 150 ml. of ether and acidified to pH 2 by adding a solution of hydrogen chloride in isopropanol. The precipitate is filtered off, washed with ether and dried to give the title hydrochloride in a yield of 8.7 g. (84.7%), m.p.; 99°–101° C. (with decomposition), $[\alpha]_D^{20} = -13.4°$ (c=1.0, chloroform).

EXAMPLE 29

Preparation of (+)-3S,16S,14R-14,15-dihydro-14-trimethoxybenzoyl-oxymethyl-eburnamenine hydrochloride [hydrochloride of a cis compound of the formula (Ia)]

The process described in Example 28 is followed, except that 6 g. of (−)-3S,16S,14R-14,15-dihydro-14-hydroxymethyl-eburnamenine are used as starting material to give the title hydrochloride in a yield of 8.05 g. (76.7%), m.p.: 110°–115° C. (with decomposition), $[\alpha]_D^{20} = +32.2°$ (c=1.0, chloroform).

EXAMPLE 30

Preparation of racemic trans-14,15-dihydro-14β-methoxycarbonyl-eburnamenine [a compound of the formula (IIIa)]

The process described in Example 1 is followed, except that 4.7 g. of racemic trans-14-methoxycarbonyl-eburnamenine are used as starting material. The solvent and the other reactants are of course used in amounts proportional to the amount of the starting eburnamenine derivative. The title compound is obtained in a yield of 4.4 g. (93%), m.p.: 182°–184° C.

EXAMPLE 31

Preparation of racemic trans-14,15-dihydro-14α-methoxycarbonyl-eburnamenine [a compound of the formula (IIIb)]

The process described in Example 2 is followed, except that 1 g. of the compound prepared according to Example 30 is used as starting material to give the title product in a yield of 0.83 g. (83%), m.p.: 117°–118° C.

EXAMPLE 32

Preparation of racemic trans-14,15-dihydro-14α-hydroxymethyl-eburnamenine [a compound of the formula (Ia)]

The process described in Example 4 is followed, except that 0.4 g. of the compound prepared according to Example 30 is used as starting material to give the title product in a yield of 0.34 g. (92.7%), m.p.: 198°–200° C.

EXAMPLE 33

Preparation of racemic trans-14,15-dihydro-14β-hydroxymethyl-eburnamenine [a compound of the formula (Ib)]

The process described in Example 4 is followed, except that 4.4 g. of the compound prepared according to Example 31 are used as starting material to give the title product in a yield of 0.33 g. (89%), m.p.: 152°–155° C.

We claim:
1. A racemic or optically active trans-eburnamenine epimer of the Formula (Ia)

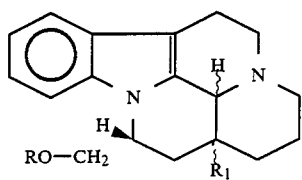

or (Ib)

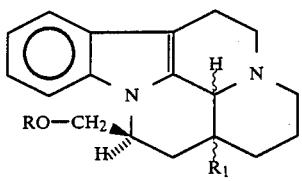

wherein
R₁ stands for a C₁ to ₄ alkyl group; and
R stands for hydrogen, or a pharmaceutically acceptable acid addition salt thereof.

2. A compound selected from the group consisting of
(−)-3S,16R,14R-14,15-dihydro-14-hydroxymethyl-eburnamenine,
(+)-3S,16R,14S-14,15-dihydro-14-hydroxymethyl-eburnamenine,
(+)-3R,16S,14R-14,15-dihydro-14-hydroxymethyl-eburnamenine and
(−)-3R,16S,14S-14,15-dihydro-14-hydroxymethyl-eburnamenine, or a pharmaceutically acceptable acid addition salt of these compounds.

3. (−)-3S,16R,14R-14,15-dihydro-14-hydroxymethyl-eburnamenine or a pharmaceutically acceptable acid addition salt thereof as defined in claim 2.

4. A pharmaceutical composition for peripheral vasodilators. which comprises as active ingredient a racemic or optically active trans eburnamenine derivative of the formula (Ia) or (Ib), as defined in claim 1 or a therapeutically useful acid addition salt thereof.

5. Method for treating mammals suffering from conditions which can be treated by a peripheral vasodilatory agent, characterized by using a therapeutically effective amount of a trans stereoisomer of a racemic or optically active eburnamenine derivative of the formula (Ia) or (Ib), as defined in claim 1, or a therapeutically useful acid addition salt thereof.

6. A process for the selective preparation of a trans epimer of the Formula (IIIa)

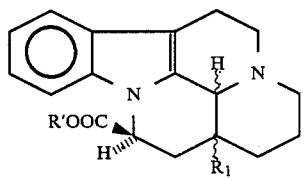

or a pharmaceutically acceptable acid addition salt thereof, wherein R₁ and R' are each C₁ to C₄ alkyl, which comprises the step of selectively catalytically hydrogenating a trans compound of the Formula (IV)

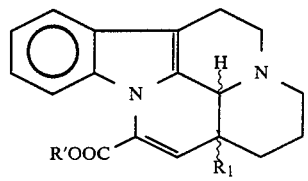

or a pharmaceutically acceptable acid addition salt thereof in the presence of a 5 to 10% palladium-on-carbon catalyst, in an alcoholic solvent at a temperature between room temperature and 60° C.

7. A process for the selective preparation of a trans epimer of the Formula (Ib)

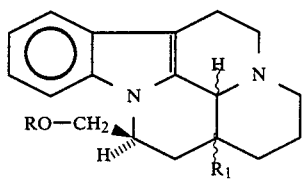

or a pharmaceutically acceptable acid addition salt thereof,
wherein
R₁ is C₁ to C₄ alkyl; and
R is hydrogen, which comprises the steps of:
(a) selectively catalytically hydrogenating a trans compound of the Formula (IV)

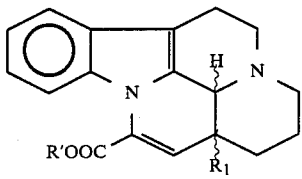

wherein R₁ and R' are each C₁ to C₄ alkyl, or a pharmaceutically acceptable acid addition salt thereof in the presence of a 5 to 10% palladium-on-carbon catalyst, in an alcoholic solvent at a temperature between room temperature and 60° C. to selectively obtain an epimer of the Formula (IIIa)

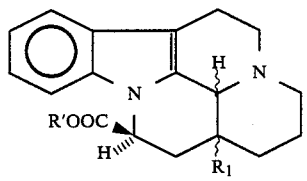

or a pharmaceutically acceptable acid addition salt thereof;
(b) epimerizing the trans compound of the Formula (IIIa) or a pharmaceutically acceptable acid addition salt thereof in an alcoholic medium in the presence of a catalytically effective amount of a basic catalyst, to selectively yield the trans epimer of the Formula (IIIb)

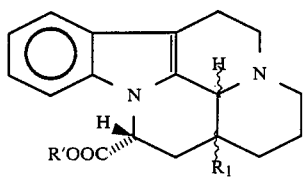
(IIIb)

or a pharmaceutically acceptable acid addition salt thereof; and (c) reducing the trans compound of the Formula (IIIb) or a pharmaceutically acceptable acid addition salt thereof with a complex metal hydride in an aprotic polar solvent to yield the trans compound of the Formula (Ib) or a pharmaceutically acceptable acid addition salt thereof.

8. A process for the selective preparation of a trans epimer of the Formula (Ia)

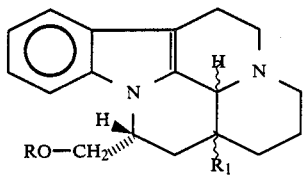
(Ia)

or a pharmaceutically acceptable acid addition salt thereof,
wherein
$R_1$ is $C_1$ to $C_4$ alkyl; and
R is hydrogen, which comprises the steps of:

(a) selectively catalytically hydrogenating a trans compound of the Formula (IV)

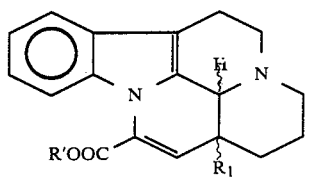
(IV)

wherein $R_1$ and $R'$ are each $C_1$ to $C_4$ alkyl, or a pharmaceutically acceptable acid addition salt thereof, in the presence of a 5 to 10% palladium-on-carbon catalyst, in an alcoholic solvent, at a temperature between room temperature and 60° C., to selectively yield a trans epimer of the Formula (IIIa)

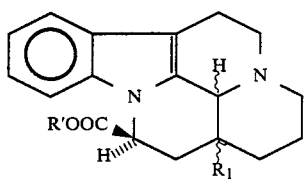
(IIIa)

or a pharmaceutically acceptable acid addition salt thereof; and (b) reducing the trans epimer of the Formula (IIIa) or a pharmaceutically acceptable acid addition salt thereof with a complex metal hydride in an aprotic polar solvent to obtain a trans epimer of the Formula (Ia) or a pharmaceutically acceptable acid addition salt thereof.

* * * * *